United States Patent
Seo et al.

(10) Patent No.: US 7,153,520 B2
(45) Date of Patent: *Dec. 26, 2006

(54) COMPOSITION FOR SUSTAINED DELIVERY OF HYDROPHOBIC DRUGS AND PROCESS FOR THE PREPARATION THEREOF

(75) Inventors: Min-Hyo Seo, Taejeon (KR); Yil-Woong Yi, Taejeon (KR); Sang-Jun Lee, Chungcheongnam-do (KR); Jae-Hong Kim, Taejeon (KR)

(73) Assignee: Samyang Corporation, Seoul (KR)

(*) Notice: Subject to any disclaimer, the term of this patent is extended or adjusted under 35 U.S.C. 154(b) by 459 days.

This patent is subject to a terminal disclaimer.

(21) Appl. No.: 10/416,980

(22) PCT Filed: Dec. 7, 2001

(86) PCT No.: PCT/KR01/02121

§ 371 (c)(1),
(2), (4) Date: May 15, 2003

(87) PCT Pub. No.: WO02/45689

PCT Pub. Date: Jun. 13, 2002

(65) Prior Publication Data

US 2004/0037885 A1   Feb. 26, 2004

(30) Foreign Application Priority Data

Dec. 7, 2000   (KR) .............................. 2000-74098

(51) Int. Cl.
*A61F 2/00* (2006.01)
(52) U.S. Cl. ............ 424/426; 424/400; 424/422; 424/423; 514/772.3; 514/772.1

(58) Field of Classification Search ............ None
See application file for complete search history.

(56) References Cited

U.S. PATENT DOCUMENTS

| | | | |
|---|---|---|---|
| 4,762,715 A | * | 8/1988 | Lukas et al. ............. 424/642 |
| 5,543,158 A | | 8/1996 | Gref et al. |
| 5,869,079 A | | 2/1999 | Wong et al. |
| 6,004,573 A | | 12/1999 | Rathi et al. |
| 6,616,941 B1 | * | 9/2003 | Seo et al. ............. 424/450 |

FOREIGN PATENT DOCUMENTS

KR   WO01/85216 A1   11/2001
KR   WO01/87345 A1   11/2001

OTHER PUBLICATIONS

S.Sweetana, et al, *Solubility Principles and Practices for Parenteral Drug Dosage Form Development*, PDA J. Pharm.Sci.&Tech.60 (1996) 330-342.

(Continued)

*Primary Examiner*—Michael P. Woodward
*Assistant Examiner*—Eric Silverman
(74) *Attorney, Agent, or Firm*—Thorpe North & Western LLP (57) ABSTRACT

A composition for the sustained delivery of a drug comprising an amphiphilic diblock copolymer; a poorly water-soluble drug; a biodegradable polymer; and liquid poly (ethylene glycol) or functional derivatives thereof and a process for preparing the composition are disclosed. When administered into a particular body site, the composition forms an implant containing the drug and drug containing polymeric micelles, which are slowly released from the implant to maintain a constant drug concentration for an extended period of time.

40 Claims, 5 Drawing Sheets

OTHER PUBLICATIONS

X. Zhang, et al, *Development of Amphiphilic Diblock Copolymers as Micellar Carriers of Taxol*, Int. J. Pharm. 132 (1996) 195-206.

So Yeon Kim, et al, *Methoxy Poly (ethylene glycol) and ∈-Caprolactone Amphiphilic Block Copolymeric Micelle Containing Indomethacin. II. Micelle formation and drug release behaviours*, J. Cont. Rel. 51 (1998) 13-22.

E. Piskin, et al, *Novel PDLLA/Peg Copolymer Micelles as Drug Carriers*, J. of Biomater. Sci. Polymer Edn. 7(4) (1995) 359-373.

* cited by examiner

Fig. 5 ated priority
COMPOSITION FOR SUSTAINED DELIVERY OF HYDROPHOBIC DRUGS AND PROCESS FOR THE PREPARATION THEREOF This application claims benefit of PCT application No. PCT/KR01/02121 filed 7 Dec. 2001 which claims a priority date of 7 Dec. 2000.

BACKGROUND OF THE INVENTION

1. Field of the Invention

The present invention relates to a composition for the sustained delivery of a hydrophobic drug and to a process for preparing the same. More specifically, the present invention relates to a liquid composition for the sustained delivery of a hydrophobic drug comprising: i) an amphiphilic diblock copolymer; ii) a hydrophobic drug; iii) a biodegradable polymer; and iv) liquid polyethylene glycol or derivatives thereof. The amphiphilic diblock copolymer forms polymeric micelles in the liquid polyethylene glycol and the hydrophobic drug is physically trapped within the micelles. Furthermore, the biodegradable polymer forms matrices in the liquid polyethylene glycol such that the drug containing micelles in the polyethylene glycol are contained within the biodegradable polymer matrices. When injected into a living body, the composition forms a polymeric implant comprising the drug containing micelles within the polymeric matrices. The micelles and drug are gradually released from the matrices and the drug is then slowly released from the micelles in a controlled manner providing for a constant drug concentration in vivo for an extended period of time.

2. Related Art

Numerous studies regarding drug delivery systems have been conducted with a variety of drugs and methods in an effort to maximize the efficacy and effects of drugs and minimize the side effects of drugs by efficient administration means and controlling the rate of drug release.

Biocompatible, biodegradable polymers have been widely used in the medical field as surgical sutures, tissue regenerative induction membranes, protective membranes for the treatment of wounds, and drug delivery systems. Among biodegradable polymers, polylactide (PLA), polyglycolide (PGA) and a copolymer (PLGA) of lactide and glycolide, are all commercially available. They have good biocompatibility and are decomposable in the body to harmless materials such as carbon dioxide, water, etc.

One example of a biodegradable polymeric drug delivery system is a system wherein a drug is contained in a biodegradable polymer matrix. These systems have the disadvantage of having to be surgically implanted. In the form of injectable drug delivery systems, polymeric microspheres and nanospheres are known in the art. However, those systems have disadvantages in that they require special preparation methods. In addition, since the biodegradable polymers used can only be dissolved in organic solvents, preparation requires the use of organic solvents harmful to the human body and therefore any residual solvent remaining after preparation of the microspheres must be completely removed. Furthermore, some drugs, such as polypeptides and proteins, may lose their physiological activity after contacting organic solvents.

Most drugs, after administration, must have a constant plasma concentration in order to provide for the desired pharmacological effects. In particular, drugs with short half-lives must be administered frequently to achieve effective plasma concentrations. For such drugs, sustained delivery formulations from which the drugs are slowly released to continuously provide their pharmacological effects, have been developed.

Many important drugs are hydrophobic and have limited solubility in water. In order to attain the expected therapeutic effect from such drugs it is usually required that a solubilized form of the drug be administered to a patient. Therefore, solubilization of a poorly water soluble drug is key technology in the preparation of a formulation for oral or parenteral, especially intravenous, administration of the drug. Common methods used for solubilization of poorly water soluble drugs are: i) dissolving the drug in a co-solvent of a water-miscible organic solvent and water; ii) modifying the drug to its salt form which is soluble in water; iii) forming a soluble drug-complex using a complexing agent; iv) introducing a hydrophilic group into the drug molecule; v) micellizing the drug in an aqueous medium with a surfactant, and vi) dispersing the drug in water to form emulsions, liposomes, nanoparticles and the like [S. Sweetana, et al., Solubility Principles and Practices for Parenteral Drug Dosage Form Development, PDA J. Pharm. Sci. & Tech. 60 (1996) 330–342].

U.S. Pat. No. 5,543,158 discloses a nanoparticle, wherein a drug is entrapped therein, formed of a block copolymer consisting of a hydrophilic polyethylene glycol block and a hydrophobic poly(lactide-co-glycolide) block. The nanoparticle has a hydrophilic outer shell that can decrease uptake of the drug by the reticuloendothelial system thus allowing it to remain in the systemic circulation for an extended period of time. However, in order to manufacture the formulation, organic solvents harmful to the human body have to be used in order to dissolve the drugs and the polymers. Furthermore, the drugs are completely exhausted from the blood within several days because they are intravascularly injected.

X. Zhang et al. reported that a polymeric micelle prepared with a diblock copolymer of poly(lactic acid) and monomethoxy poly(ethylene glycol) was useful as a carrier of paclitaxel [X. Zhang et al., Int. J. Pharm. 132 (1996) 195–206], and Shin et al. disclose a solubilization method for indomethacin using a diblock copolymer of poly(ethylene glycol) and polycaprolactone [I. Gyun Shin et al., J. Contr. Rel. 51 (1998) 13–22]. In these methods, a poorly water soluble drug is incorporated in a polymeric micelle, wherein the polymers are biocompatible and biodegradable. According to their methods, a drug and a block copolymer are dissolved together in an organic solvent, especially in a water-miscible organic solvent such as tetrahydrofuran or dimethyl formamide. The polymeric micelles are prepared by dialyzing the solution in water first and then freeze-drying the aqueous micellar solution. Alternatively, a solution of a polymer and drug in a water-miscible organic solvent, acetonitrile, is prepared. The organic solvent is slowly evaporated to give a homogeneous drug-polymer matrix and the matrix is then dispersed in an aqueous medium at ca. 60° C. to form the polymeric micelles.

Implants can be directly applied to a particular body site rather than being intravascularly injected. For example, U.S. Pat. No. 5,869,079 discloses an implant comprising the poorly water-soluble drug dexamethasone, a copolymer of lactic acid and glycolic acid, and hydroxypropyl methylcellulose. In addition, U.S. Pat. No. 6,004,573 discloses that a PLGA-PEG-PLGA triblock copolymer made up of hydrophobic poly(lactide-co-glycolide) (PLGA) blocks and a hydrophilic polyethylene glycol (PEG) block can be used as an implant for effectively delivering poorly water-soluble drugs. However, the above formulations fail to provide for effective plasma concentrations of poorly water-soluble drugs due to their extremely low solubility in body fluids. Thus, a composition for use as an implant that can be prepared by a simple procedure, and which releases the hydrophobic drug over an extended period of time and which is administered by a single injection and then decomposes into materials harmless to human body, is needed.

SUMMARY OF THE INVENTION

It has been recognized that it would be advantageous to develop a composition for the sustained delivery of a hydrophobic drug that is capable of forming an implant when administered into a particular body site.

The present invention provides a composition for the sustained delivery of a hydrophobic drug that forms an implant when administered into a particular body site and the drug and polymeric micelles containing the drug are slowly released, in vivo, from the implant.

One aspect of the present invention relates to a composition for the sustained delivery of a poorly water-soluble drug comprising: i) an amphiphilic diblock copolymer; ii) a poorly water-soluble drug; and iii) a biodegradable polymer, dispersed or suspended in liquid poly(ethylene glycol) or a suitable derivative thereof.

According to the present invention, the amphiphilic diblock copolymer forms polymeric micelles in the liquid polyethylene glycol and the poorly water-soluble drug is trapped within the polymeric micelles. In addition, when administered into the body, the biodegradable polymer develops into an implant by forming matrices in the liquid polyethylene glycol. The drug and polymeric micelles containing the drug are slowly released in vivo from the implant matrices over sustained periods of time and the polymers then decompose into materials harmless to the human body.

The amphiphilic diblock copolymer in the present invention is preferably a diblock copolymer of a hydrophilic poly(alkylene glycol) block and a hydrophobic biodegradable polymer block dispersed or suspended in a poly(ethylene glycol) matrix, or its derivatives.

The term poly(ethylene glycol) or PEG, as used herein, shall also be deemed to include derivatives of PEG unless otherwise specifically stated. Such derivatives will be more specifically described in the disclosure that follows. Since only the hydrophilic component block, not the hydrophobic component block, of the copolymer has an affinity or attraction for the poly(ethylene glycol) matrix, the block copolymer forms a core-shell structure wherein the hydrophobic biodegradable polymer block occupies the inner core and the hydrophilic poly(alkylene glycol) block forms the outer shell in the poly(ethylene glycol) medium. In addition, the biodegradable polymer employed in the present invention forms matrices in liquid polyethylene glycol and controls the release rate of the hydrophobic drug and the drug containing polymeric micelles.

The content of the amphiphilic diblock copolymer is preferably within the range of 3 to 70% by weight and more preferably from 5 to 50% by weight, based on the total weight of the composition. The drug content is within the range of 0.1 to 50% by weight and is preferably 1 to 30% by weight, based on the weight of the amphiphilic diblock copolymer. The content of the biodegradable polymer is within the range of 5 to 80% by weight and is preferably 10 to 70% by weight, based on the total weight of the composition. The molecular weight of the biodegradable polymer is within the range of 500 to 50,000 Daltons and is preferably from 1,000 to 30,000 Daltons. The content of liquid polyethylene glycol employed in the present invention is within the range of 5 to 80% by weight and is preferably from 10 to 60% by weight, based on the total weight of the composition.

The composition of the present invention forms implants when administered into a particular body site, and the drug and polymeric micelles containing the same are slowly released therefrom. Therefore, a constant concentration of the drug is kept at the administration site as well as in the circulation thereby achieving excellent pharmacological effects. Also, no organic solvent harmful to the human body is involved in the composition or the preparation process thereof. Moreover, the polymers employed in the present invention are safely degraded into products harmless to the human body and are then excreted.

Additional features and advantages of the invention will be apparent from the detailed description which follows, taken in conjunction with the accompanying drawings, which together illustrate, by way of example, features of the invention.

DETAILED DESCRIPTION

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention relates to a composition for the sustained delivery of a poorly water-soluble drug comprising: i) an amphiphilic diblock copolymer; ii) a poorly water-soluble drug; and iii) a biodegradable polymer, dispersed or suspended in liquid poly(ethylene glycol). When injected into a living body, the composition of the present invention forms a polymeric implant which contains a poorly water soluble drug and drug-containing micelles. The drug and the drug containing micelles are slowly released over a prolonged period of time and the polymers are decomposed into materials harmless to the human body.

The block copolymer portion of such compositions has a core-shell structure wherein the hydrophobic biodegradable polymer block occupies the inner core and the hydrophilic poly(alkylene glycol) block forms the outer shell in the hydrophilic liquid poly(ethylene glycol) matrix or medium. The poly(ethylene glycol) functions as a dispersant to facilitate water solubility and the block copolymer portion of the composition forms a micellular structure in body fluids or in an aqueous medium. When a poorly water soluble drug is added to the composition, it is contained within the inner hydrophobic core. Accordingly, a pharmaceutical formulation containing the composition of the present invention is capable of effectively solubilizing a poorly water soluble drug in a body fluid or in an aqueous medium by forming a micelle, wherein the drug is entrapped in the core of the micelle. In addition, the biodegradable polymer employed in the present invention forms matrices in liquid polyethylene glycol which controls the release rate of the hydrophobic drug and polymeric micelles containing the hydrophobic drug, from the implant site into the body.

In summary, the present invention is a combination of an amphiphilic diblock copolymer and a biodegradable polymer, as defined herein, suspended in a liquid poly(ethylene glycol) medium. The amphiphilic diblock copolymer comprises a hydrophilic poly(alkylene glycol) component and a hydrophobic biodegradable polymer component. The poly(ethylene glycol) medium facilitates the dispersion of the diblock copolymer which forms a polymeric micelle. When a poorly water soluble drug is added to the composition, the drug is solubilized by incorporating the drug into the inner core of the micelle. The composition of the present invention forms a polymeric implant when injected into a living body, from which the drug and the drug-containing micelles are slowly released over a prolonged period of time and the implant is then decomposed into materials harmless to the human body and excreted.

The polyalkylene glycol suitable for the hydrophilic component of the amphiphilic diblock copolymer of the present invention is a member selected from the group consisting of polyethylene glycol, monoalkoxy polyethylene glycol, or monoacyloxy polyethylene glycol wherein the molecular weight of the polyalkylene glycol is preferably within the range of 500~20,000 Daltons, and more preferably within the range of 1,000~15,000 Daltons. The content of the hydrophilic component of the amphiphilic diblock copolymer is within the range of 30~80 wt %, preferably 40~70 wt %, based on the total weight of the block copolymer.

The hydrophobic biodegradable polymer component of the amphiphilic diblock copolymer of the present invention is a member selected from the group consisting of polylactides, polycaprolactone, copolymers of lactide and glycolide, copolymers of lactide and caprolactone, copolymers of lactide and 1,4-dioxan-2-one, polyorthoesters, polyanhydrides, polyphosphazines, poly(amino acid)s and polycarbonates. Preferably, the hydrophobic biodegradable polymer component of the copolymer of the present invention is a member selected from the group consisting of polylactides, polycaprolactone, a copolymer of lactide and glycolide, a copolymer of lactide and caprolactone, and a copolymer of lactide and 1,4-dioxan-2-one. The molecular weight of the hydrophobic biodegradable polymer component is preferably within the range of 500~20,000 Daltons, and more preferably within the range of 1,000~15,000 Daltons.

The amphiphilic diblock copolymer of the present invention can be synthesized by polymerizing lactone type heterocyclic esters and monoalkoxypolyethylene glycols at a temperature of 80 to 130° C. using stannous octoate ($SnOct_2$) as a catalyst [E. Piskin et al., Novel PDLA/PEG copolymer micelles as drug carriers, J. of Biomater. Sci. Polymer Edn. 7 (4) (1995) 359–373]. For example, they may be prepared via ring opening bulk polymerization of one of the cyclic ester monomers, such as lactide, glycolide, or 1,4-dioxan-2-one with monomethoxy poly(ethylene glycol) (mPEG) or poly (ethylene glycol) (PEG) in the presence of stannous octoate as a catalyst at 80~130° C. When the 1,4-dioxan-2-one is used as the monomer, the preferable reaction temperature is 80~110° C. When a copolymer of 1,4-dioxan-2-one and lactide is used, the 1,4-dioxan-2-one monomer is first reacted with mPEG or PEG at 100~130° C., the lactide monomer is then slowly added to increase the degree of polymerization of 1,4-dioxan-2-one. Since the conversion of the 1,4-dioxan-2-one monomer is 50~60%, the added amount of this monomer should be more than the calculated amount when the two monomers, 1,4-dioxan-2-one and lactide, are added together. The block copolymer product is dissolved in dichloromethane or acetone, precipitated in diethyl ether, hexane, pentane, or heptane, followed by drying.

The liquid poly(ethylene glycol) or its derivatives, used as a dispersion medium for the composition of the present invention, have high attraction for the hydrophilic component of the diblock copolymer and preferably, have melting temperature of below about 40° C., and molecular weights of 100~3,000 Daltons and more preferably 200~2,000 Daltons. The term "liquid" used herein is defined as the liquid phase at a temperature of 50° C. Accordingly, the liquid polyethylene glycol employed in the present invention may be one or more selected from the group consisting of polyethylene glycol, and alkyl or allyl derivatives thereof, each of which is liquid at 50° C.

Figure 1:
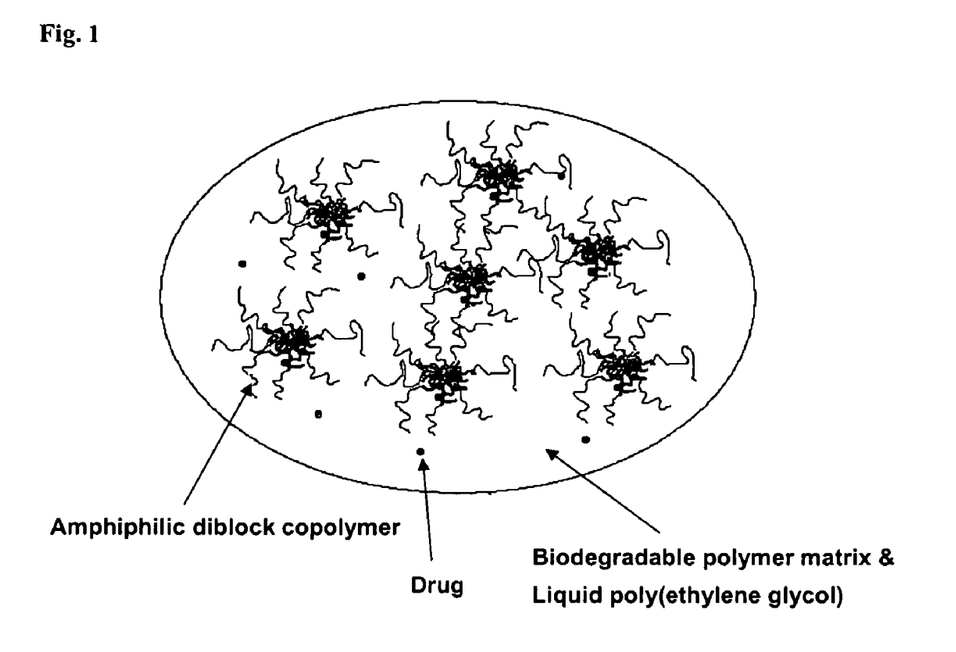
FIG. 1 is a schematic representation of the composition of the present invention.

As shown in FIG. 1, the biodegradable polymer employed in the present invention forms matrices in liquid polyethylene glycol and controls the rate of release of the drug and polymeric micelles containing the same. The biodegradable polymer employed in the present invention should be biocompatible, be degradable into products harmless to the human body after a given time in vivo, and be soluble or uniformly dispersible in liquid polyethylene glycol of low molecular weight. Examples of the biodegradable polymer include polylactide, polycaprolactone, poly(lactide-co-glycolide) and mixtures thereof. The content of the biodegradable polymer is within the range of 5 to 80% by weight and preferably from 10 to 70% by weight, based on the total weight of the composition. The molecular weight of the biodegradable polymer is within the range of 500 to 50,000 Daltons and is preferably from 1,000 to 30,000 Daltons.

The content of the amphiphilic diblock copolymer is preferably within the range of 3 to 70% by weight and more preferably is from 5 to 50% by weight, based on the total weight of the composition. The drug content is within the range of 0.1 to 50% by weight and preferably from 1 to 30% by weight, based on the weight of the amphiphilic diblock copolymer. The content of the biodegradable polymer is within the range of 5 to 80% by weight and is preferably from 10 to 70% by weight, based on the total weight of the composition. The content of liquid polyethylene glycol employed in the present invention is within the range of 5 to 80% by weight and is preferably from 10 to 60% by weight, based on the total weight of the composition.

Figure 2:
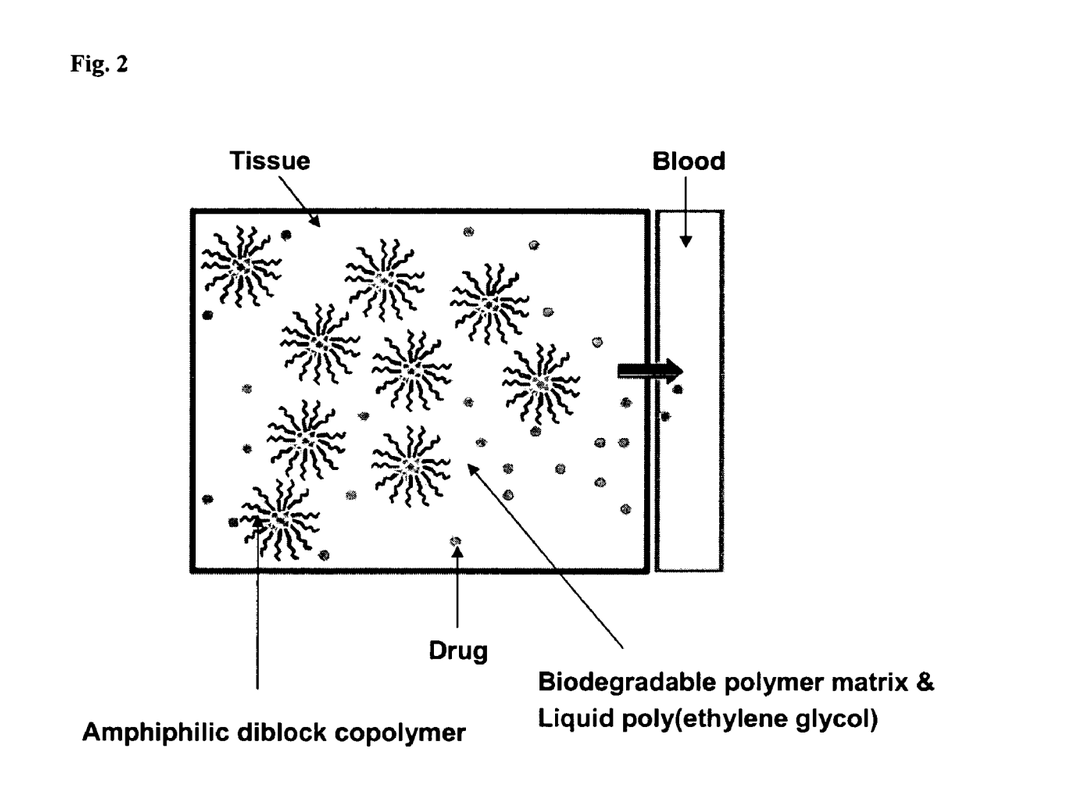
FIG. 2 schematically illustrates drug release from a tissue implant formed when the composition of the present invention is injected into the body.

When introduced into the body, the composition of the present invention forms an implant. As illustrated in FIG. 2, the poorly water-soluble drugs are entrapped within the polymeric micelles formed by the amphiphilic diblock copolymer which in turn are embedded in the biodegradable polymer matrix and the liquid polyethylene glycol (PEG) medium. Therefore, the drugs and/or drug-containing micelles are slowly released from the polymeric micelles and/or from the implant thereby providing a constant drug circulation concentration for an extended period of time. Thus the compositions of the present invention are especially useful for the sustained delivery of poorly water soluble drugs having solubilities of less than 10 mg/mL at ambient temperatures. Examples of these hydrophobic drugs include anticancer agents, antiinflammatory agents, antifungal agents, antiemetics, antihypertensive agents, sex hormones, and steroids. Typical examples of these hydrophobic drugs are: anticancer agents such as paclitaxel, docetaxel, camptothecin, doxorubicin, daunomycin, cisplatin, 5-fluorouracil, mitomycin, methotrexate, and etoposide; antiinflammatory agents such as indomethacin, ibuprofen, ketoprofen, flubiprofen, dichlofenac, piroxicam, tenoxicam, naproxen, aspirin, and acetaminophen; antifungal agents such as itraconazole, ketoconazole and amphotericin; sex hormons such as testosterone, estrogen, progesterone, and estradiol; steroids such as dexamethasone, prednisolone, betamethasone, triamcinolone acetonide and hydrocortisone; antihypertensive agents such as captopril, ramipril, terazosin, minoxidil, and parazosin; antiemetics such as ondansetron and granisetron; antibiotics such as metronidazole, and fusidic acid; cyclosporines; prostaglandins; and biphenyl dimethyl dicarboxylic acid.

The rate of release of a drug and of the polymeric micelles containing the same, depends on the composition of the biodegradable polymer and the molecular weight and content thereof, because the degradation rate depends on the kind of polymer employed and the viscosity of the matrix depends on the molecular weight and content of the polymer employed.

Since the composition of the present invention contains a biocompatible polymer which is degradable after a given time into products that are harmless to the human body and is excreted from the body, the drug release rate can be controlled by adjusting the content of each component. The composition forms implants when injected into a particular body site, the drug and the polymeric micelles containing the same, are slowly released from the implants, thereby keeping a constant concentration of the drug at the implantation site as well as in the circulation for an extended period of time. Therefore, the composition of the present invention can provide for excellent pharmacological effects. That is, as shown in the following Example 19 (drug release test), in a composition without the amphiphilic diblock copolymer (Comparative Example 1), only an extremely small amount of the drug is released into an aqueous medium. In a composition without the biodegradable polymeric matrix (Comparative Example 2), the drug is completely released into the aqueous medium within 24 hours. By contrast, the present composition can control the release of the drug and the polymeric micelles containing the same, by adjusting the content of each component. Therefore, the present composition provides for a constant concentration of the drug for an extended period of time.

The composition of the present invention may be prepared as follows. An amphiphilic diblock copolymer, and a poorly water-soluble drug are mixed in liquid polyethylene glycol and stirred to prepare a polymeric micellar composition (Composition A) containing the poorly water-soluble drug entrapped therein. In the above process, the stirring is carried out, preferably at a temperature of 40 to 80° C., for 30 to 60 minutes. A biodegradable polymer is dissolved or dispersed in liquid polyethylene glycol to prepare Composition B. Then, Composition A is mixed with Composition B and stirred to prepare a composition for the sustained delivery of a drug of the present invention. In the above process the stirring is carried out, preferably at a temperature of 40 to 80° C., for 1 to 2 hours.

The composition of the present invention may be injected into a particular site of the human body by means of a syringe or catheter. The polymers contained in the present composition are safe in that the United States Food and Drug Administration (FDA) has allowed them for in vivo use. The polymers have the additional advantage in that they are hydrolyzed into products readily excreted from the body.

While the following preparations and examples are provided for the purpose of illustrating certain aspects of the present invention, they are not to be construed as limiting the scope of the appended claims.

EXAMPLES

Synthesis of Amphiphilic Diblock copolymer

Preparation 1: mPEG-PLA (MW 2,000–1,800)

25 g of methoxypolyethylene glycol (MPEG, MW=2,000) and 25 g of D,L-lactide recrystallized from ethyl acetate were added to a round-bottomed flask equipped with a pedal stirrer. Thereto was added 0.25 g of stannous octoate ($SnOct_2$) dissolved in 5 ml of toluene. The flask was then heated to 120° C. in an oil bath to evaporate excess toluene. Subsequently, the reaction was performed under reduced pressure (25 mmHg) for 6 hours. The resulting product was dissolved in chloroform. The solution was slowly added to cold diethyl ether (4° C.) to precipitate the formed polymer. The polymer was purified by repeating the dissolution-precipitation process twice and was then dried in a vacuum oven (0.1 mmHg) for 24 hours. The molecular weight of the copolymer (mPEG-PLA) was identified by Nuclear Magnetic Resonance (NMR) Spectroscopy.

Preparation 2: mPEG-PLA (MW 3,400–2,500)

According to substantially the same method as in Preparation 1, a copolymer (mPEG-PLA) was prepared using 25 g of methoxypolyethylene glycol (mPEG, MW=3,400), 20 g of D,L-lactide, and 0.20 g of stannous octoate, and the molecular weight of the copolymer was identified.

Preparation 3: mPEG-PLA (MW 5,000–4,000)

According to substantially the same method as in Preparation 1, a copolymer (mPEG-PLA) was prepared using 25 g of methoxypolyethylene glycol (mPEG, MW=5,000), 22 g of D,L-lactide, and 0.22 g of stannous octoate, and the molecular weight of the copolymer was identified.

Preparation 4: mPEG-PLA (MW 8,000–6,000)

According to substantially the same method as in Preparation 1, a copolymer (mPEG-PLA) was prepared using 25 g of methoxypolyethylene glycol (mPEG, MW=8,000), 20 g of D,L-lactide, and 0.20 g of stannous octoate, and the molecular weight of the copolymer was identified.

Preparation 5: MPEG-PCL (MW 5,000–4,000)

According to substantially the same method as in Preparation 1, a copolymer (mPEG-PCL) was prepared using 25 g of methoxypolyethylene glycol (mPEG, MW=5,000), 20 g of ε-caprolactone, and 0.20 g of stannous octoate, and the molecular weight of the copolymer was identified.

Preparation 6: mPEG-PLGA (MW 5,000–4,000, LA/GA=7/3)

According to substantially the same method as in Preparation 1, a copolymer (mPEG-PLGA) was prepared using 25 g of methoxypolyethylene glycol (mPEG, MW=5,000), 15 g of D,L-lactide, 7 g of glycolide and 0.22 g of stannous octoate, and the molecular weight of the copolymer was identified.

Preparation 7: mPEG-PLDO (MW 5,000–4,000, LA/DO=7/3)

According to substantially the same method as in Preparation 1, a copolymer (mPEG-PLDO) was prepared using 25 g of methoxypolyethylene glycol (mPEG, MW=5,000), 15 g of D,L-lactide, 7 g of 1-p-dioxanone and 0.22 g of stannous octoate, and the molecular weight of the copolymer was identified.

Preparation of Biodegradable Polymer Controlling Release Rate

Preparation 8: PLA (MW 4,000)

30 g of lactic acid was added to a round-bottomed flask equipped with a pedal stirrer. Thereto was added 0.15 g of antimony oxide ($Sb_2O_3$). The flask was equipped with a distillation tube, and the temperature was slowly increased. The reaction was performed at 160° C. for 10 hours. Subsequently, the reaction was further performed under reduced pressure (25 mmHg) for an additional 6 hours. The resulting product was dissolved in chloroform. The solution was slowly added to cold diethyl ether (4° C.) to precipitate the formed polymer. The polymer was purified by repeating the dissolution-precipitation process twice and then the polymer was dried in a vacuum oven (0.1 mmHg) for 24 hours. The molecular weight of the polymer (PLA) was identified by Nuclear Magnetic Resonance (NMR) Spectroscopy.

Preparation 9: PLGA (MW 4,000, LA/GA=7/3)

According to substantially the same method as in Preparation 8, a PLGA polymer was prepared using 21 g of lactic acid and 9 g of glycolic acid, and the molecular weight of the copolymer was identified.

Preparation of Drug Composition

Example 1

Paclitaxel Containing Composition

In a round-bottomed flask equipped with a pedal stirrer were mixed 90 mg of the amphiphilic diblock copolymer (mPEG-PLA) prepared in Preparation 1, 10 mg of paclitaxel as a poorly water-soluble drug and 100 mg of a liquid polyethylene glycol (PEG, MW 300). The mixture was then stirred at 60° C. for 30 minutes to prepare Composition A. According to the same method as above, 100 mg of polylactide (PLA, MW 4,000) as a biodegradable polymer that forms matrices, was dissolved in 100 mg of the same polyethylene glycol used to prepare Composition B. Composition A was mixed with Composition B and stirred at 60° C. for 1 hour to prepare a transparent viscous liquid composition.

Examples 2 to 18

Poorly water-soluble drug containing compositions were prepared using the ingredients and the contents as listed in Table 1 below, according to substantially the same method as in Example 1.

Comparative Examples 1 and 2

Poorly water-soluble drug containing compositions were prepared using the ingredients and the contents as listed in Table 1 below.

TABLE 1

| | Amphiphilic diblock copolymer | Drug | PEG | Polymeric matrix* |
|---|---|---|---|---|
| Example 1 | mPEG-PLA (MW 2,000–1,800) 90 mg | Paclitaxel 10 mg | PEG (MW 300) 200 mg | PLA 100 mg |
| Example 2 | mPEG-PLA (MW 2,000–1,800) 90 mg | Paclitaxel 10 mg | PEG (MW 300) 300 mg | PLA 100 mg |
| Example 3 | mPEG-PLA (MW 2,000–1,800) 90 mg | Paclitaxel 10 mg | PEG (MW 600) 400 mg | PLA 300 mg |
| Example 4 | mPEG-PLA (MW 2,000–1,800) 90 mg | Paclitaxel 10 mg | PEG (MW 600) 400 mg | PLA 600 mg |
| Example 5 | mPEG-PLA (MW 3,400–2,500) 90 mg | Paclitaxel 10 mg | PEG (MW 300) 400 mg | PLA 300 mg |
| Example 6 | mPEG-PLA (MW 3,400–2,500) 90 mg | Paclitaxel 10 mg | PEG (MW 300) 400 mg | PLA 600 mg |
| Example 7 | mPEG-PLA (MW 3,400–2,500) 90 mg | Paclitaxel 10 mg | PEG (MW 300) 400 mg | PLA 900 mg |
| Example 8 | mPEG-PLA (MW 3,400–2,500) 90 mg | Paclitaxel 10 mg | PEG (MW 300) 400 mg | PLA 1,200 mg |
| Example 9 | mPEG-PLA (MW 3,400–2,500) 90 mg | Paclitaxel 10 mg | PEG (MW 300) 600 mg | PLA 1,200 mg |
| Example 10 | mPEG-PLA (MW 3,400–2,500) 90 mg | Paclitaxel 10 mg | PEG (MW 600) 400 mg | PLA 600 mg |
| Example 11 | mPEG-PLA (MW 3,400–2,500) 90 mg | Paclitaxel 10 mg | PEG (MW 800) 400 mg | PLA 600 mg |
| Example 12 | mPEG-PLA (MW 3,400–2,500) 95 mg | Paclitaxel 5 mg | PEG (MW 300) 400 mg | PLGA 600 mg |
| Example 13 | mPEG-PLA (MW 3,400–2,500) 90 mg | Indomethacin 10 mg | PEG (MW 300) 400 mg | PLA 600 mg |
| Example 14 | mPEG-PLA (MW 3,400–2,500) 90 mg | Indomethacin 10 mg | PEG (MW 300) 400 mg | PLA 900 mg |
| Example 15 | mPEG-PLA (MW 5,000–4,000) 80 mg | Indomethacin 20 mg | PEG (MW 800) 400 mg | PLA 900 mg |
| Example 16 | mPEG-PCL (MW 5,000–4,000) 80 mg | Indomethacin 20 mg | PEG (MW 300) 400 mg | PLA 900 mg |
| Example 17 | mPEG-PLGA (MW 5,000–4,000, LA/GA = 7/3) 90 mg | Cyclosporine A 10 mg | PEG (MW 300) 400 mg | PLA 600 mg |
| Example 18 | mPEG-PLDO (MW 5,000–4,000, LA/DO = 7/3) 95 mg | Paclitaxel 5 mg | PEG (MW 300) 400 mg | PLA 300 mg |
| Comparative Example 1 | — | Paclitaxel 10 mg | PEG (MW 600) 400 mg | PLA 300 mg |
| Comparative Example 2 | mPEG-PLA (MW 2,000–1,800) 90 mg | Paclitaxel 10 mg | PEG (MW 600) 400 mg | — |

*PLA: Poly(lactide) (MW 4,000);
PLGA: Poly(lactide-co-glycolide) (MW 4,000, LA/GA = 7/3)

Example 19

Drug Release Test 500 mg of each composition obtained from Examples 1 to 18 and Comparative Examples 1 and 2 were added to a capped test tube. Thereto was then added 15 ml of physiological saline. The composition solidified at the bottom was transferred into a chamber at 37° C. The physiological saline was completely refreshed at regular intervals. An aqueous solution containing the released drug was centrifuged and the drug was extracted from the supernatant with methylene chloride. This solution was dried and the product was redissolved in a 40% aqueous acetonitrile solution. The concentration of the drug was then measured by HPLC. The results are shown in the following Table 2 and FIG. 3.

TABLE 2

| | \multicolumn{6}{c}{Cumulative Release Rate (%)} | | | | | |
|---|---|---|---|---|---|---|
| | 0 day | 1 day | 2 days | 3 days | 5 days | 7 days | 10 days |
| Example 1 | 0 | 33 | 40 | 54 | 65 | 72 | 85 |
| Example 2 | 0 | 36 | 47 | 57 | 68 | 76 | 90 |
| Example 3 | 0 | 31 | 40 | 51 | 62 | 70 | 82 |
| Example 4 | 0 | 23 | 33 | 45 | 53 | 65 | 70 |
| Example 5 | 0 | 25 | 36 | 45 | 57 | 68 | 78 |
| Example 6 | 0 | 21 | 35 | 42 | 48 | 57 | 65 |
| Example 7 | 0 | 18 | 28 | 37 | 42 | 49 | 53 |
| Example 8 | 0 | 17 | 24 | 33 | 38 | 42 | 45 |
| Example 9 | 0 | 18 | 30 | 40 | 45 | 53 | 57 |
| Example 10 | 0 | 21 | 31 | 42 | 47 | 57 | 62 |
| Example 11 | 0 | 20 | 31 | 40 | 47 | 55 | 60 |
| Example 12 | 0 | 23 | 34 | 46 | 51 | 62 | 69 |
| Example 13 | 0 | 23 | 33 | 45 | 55 | 65 | 71 |
| Example 14 | 0 | 17 | 31 | 38 | 47 | 53 | 58 |
| Example 15 | 0 | 17 | 25 | 33 | 38 | 45 | 50 |
| Example 16 | 0 | 18 | 28 | 35 | 43 | 49 | 55 |
| Example 17 | 0 | 19 | 30 | 38 | 47 | 53 | 57 |
| Example 18 | 0 | 18 | 31 | 38 | 49 | 55 | 60 |
| Comparative Example 1 | 0 | 2 | 2 | 3 | 3 | 3 | 4 |
| Comparative Example 2 | 0 | 100 | — | — | — | — | — |

Figure 3:
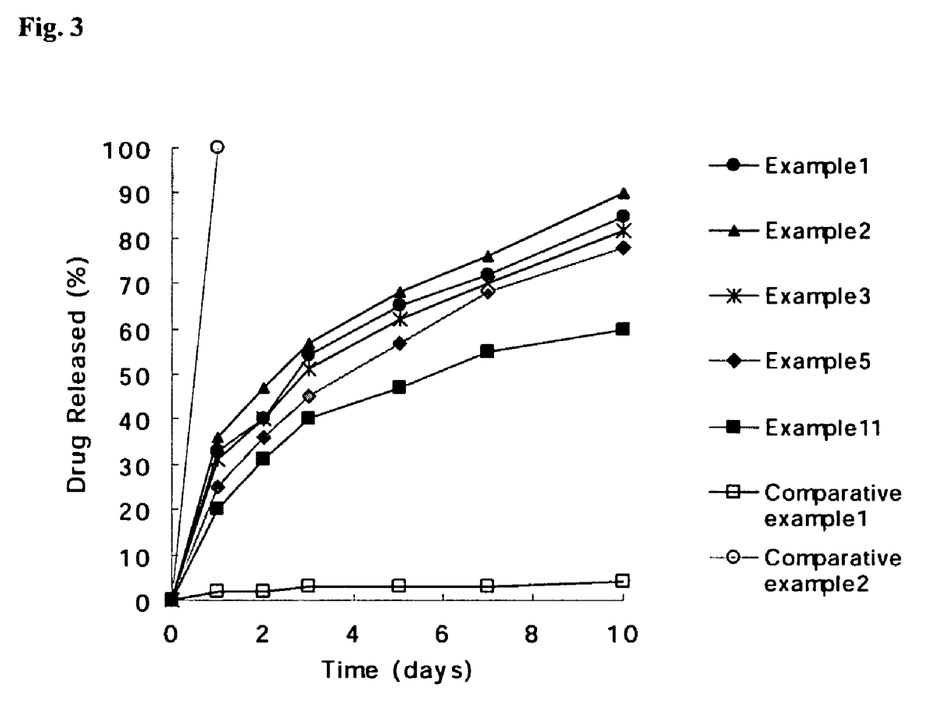
FIG. 3 illustrates the results of in vitro drug release tests for the composition of the present invention.

As shown in Table 2 and FIG. 3, the drug release rate can be controlled depending on the content of each ingredient in the present composition. By contrast, in a composition without an amphiphilic diblock copolymer (Comparative Example 1), almost no drug was released into the aqueous medium. Additionally, in a composition without a biodegradable polymeric matrix (Comparative Example 2), the drug was completely released into the aqueous medium within 24 hours.

Example 20

Anticancer Activity on Ovarian Cancer

In preparing animals to be used in the anticancer activity test, a piece of human ovarian cancer (SKOV-3, 3–4 mm) was xenografted onto the right side of female nude mice (Balb/c, an age of 5–6 weeks, a body weight of 19–21 g) using a 12 gauge troika. When the volume of the grafted cancer tissue grew to 300–500 mm$^3$, the composition prepared in Example 1, which was sterilized using a 0.22 μm filter under aseptic conditions, was injected intratumorally using a 26-gauge syringe needle. For comparison, a commercially available paclitaxel formulation, which is made by dissolving 6 mg of paclitaxel and 527 mg of Cremophor® EL in 1 ml ethanol/water (1:1, v/v), was used intravenously.

Figure 4:
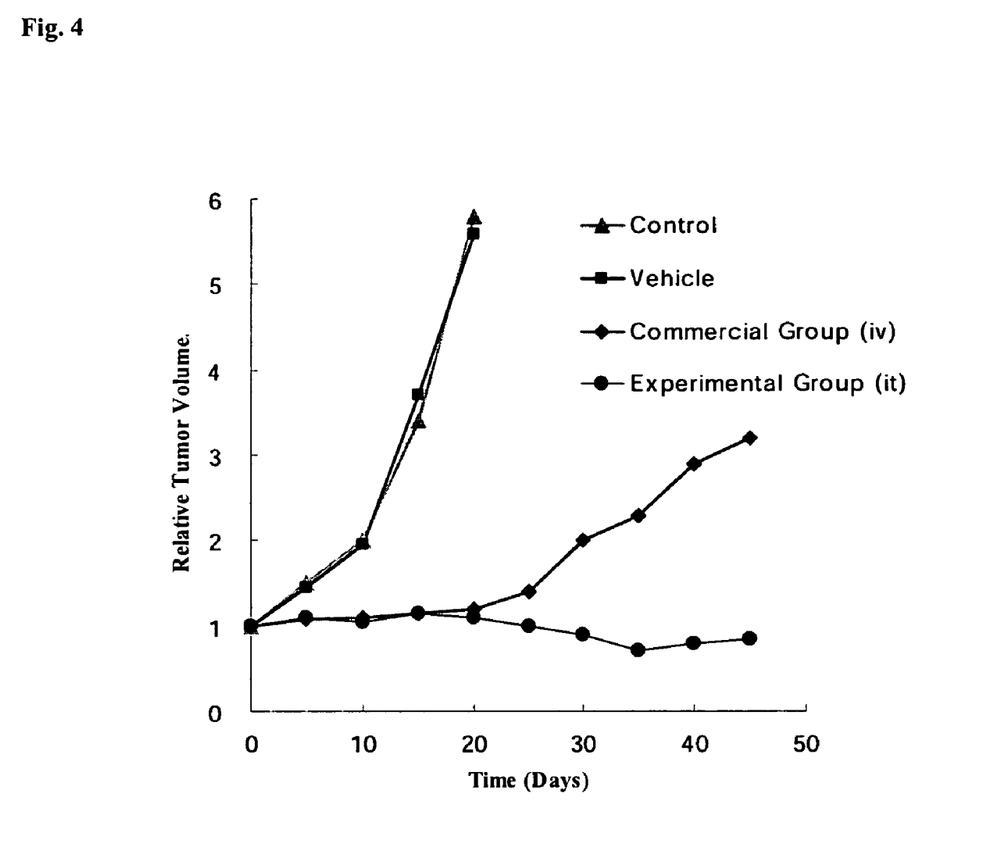
FIG. 4 illustrates the anticancer activity of the paclitaxel-containing composition of the present invention against human ovarian cancer; and, FIG. 5 illustrates the anticancer activity of the paclitaxel-containing composition of the present invention against human prostatic carcinoma.

The composition of the present invention (Example 1) was injected once at a dose of 20 mg/kg (day 0). The commercial formulation was administered into the tail vein three times (once on days 0, 1 and 2) at a dose of 20 mg/kg. During administration, the cancer tissue was measured on the long and short axes at 5-day intervals. The volume of cancer tissue was calculated by the formula $\pi/6((L+W)/2)^3$ wherein W represents the length of the long axis and L represents the length of the short axis. The compositions of the administered formulations are shown in the following Table 3. The volume ratio (relative volume) of the cancer tissue upon administration and at given times after administration is shown in FIG. 4.

TABLE 3

| | Composition | Administration route* | Dose | No. of mice |
|---|---|---|---|---|
| Control | — | No treatment | — | 6 |
| Vehicle | Composition of Example 1 without drug | it | — | 6 |
| Commercial Formulation (iv) | Composition of the commercial formulation | iv | 20 mg/kg × 3 | 6 |
| Experimental Group (it) | Composition of Example 1 | it | 20 mg/kg | 6 |

*it: intratumoral,
iv: intravenous

Example 21

Anticancer Activity Against Prostatic Carcinoma

Figure 5:
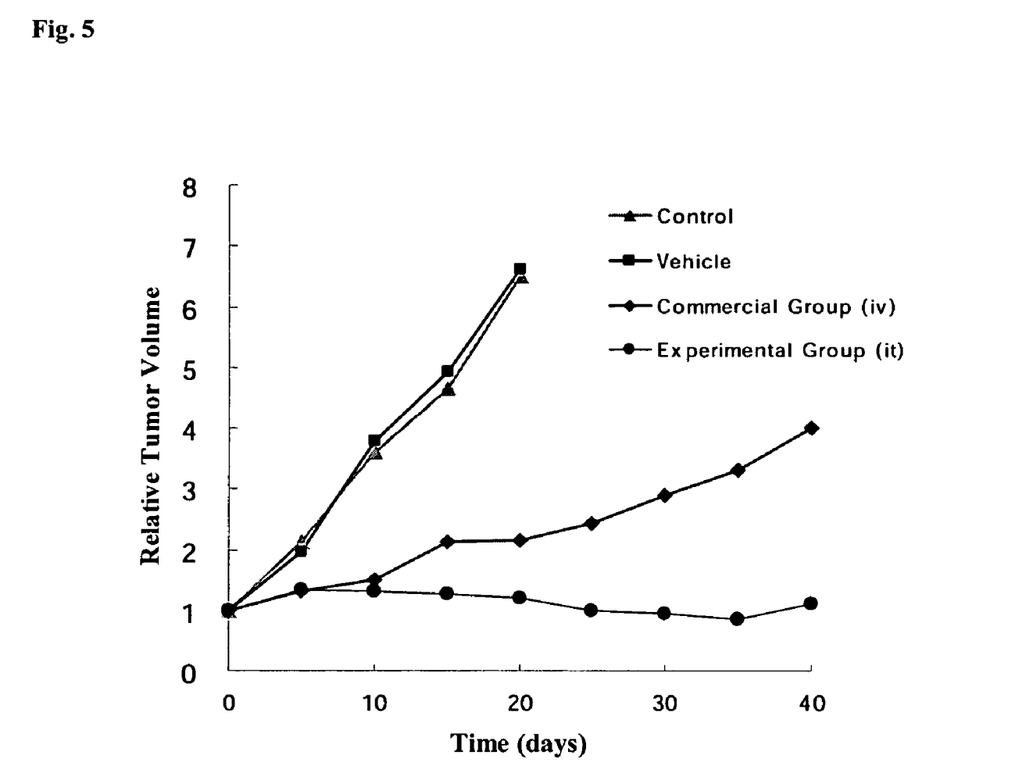

A piece of human prostatic carcinoma (PC-3, 3–4 mm) was transplanted onto the right side of male nude mice (Balb/c of 5–6 weeks, 19–21 g). The anticancer activity test was then carried out according to substantially the same method as in Example 20. The compositions of the administered formulations are shown in Table 4 below. The volume ratio (relative volume) of the cancer tissue upon administration and at given times after administration is shown in FIG. 5.

TABLE 4

| | Composition | Administration route* | Dose | No. of mice |
|---|---|---|---|---|
| Control | — | No treatment | — | 6 |
| Vehicle | Composition of Example 1 without drug | it | — | 6 |
| Commercial Formulation (iv) | Composition of the commercial formulation | iv | 20 mg/kg × 3 | 6 |
| Experimental Group (it) | Composition of Example 1 | it | 60 mg/kg | 6 |

*it: intratumoral,
iv: intravenous

As shown in FIGS. 4 and 5, the paclitaxel-containing composition of the present invention exhibits much higher anticancer activity than the known formulation.

It is to be understood that the above-referenced arrangements are illustrative of application of the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A liquid polymeric composition for the sustained delivery of a poorly water-soluble drug comprising:
    i) an amphiphilic diblock copolymer;
    ii) a poorly water-soluble drug;
    iii) a biodegradable polymer; and, iv) liquid poly(ethylene glycol); wherein said amphiphilic diblock copolymer, said poorly water-soluble drug and said biodegradable polymer are dissolved or dispersed in said liquid poly(ethylene glycol); and wherein said composition is an injectable liquid at a room temperature and, upon being injected into a body, forms an implant containing polymeric micelles wherein said poorly water-soluble drugs are physically trapped and wherein said amphiphilic diblock copolymer is composed of a hydrophilic polyalkylene glycol block selected from the group consisting of polyethylene glycol, monoalkoxypolyethylene glycol and monoacyloxypolyethylene glycol and a hydrophobic biodegradable polymer block selected from the group consisting of polylactides, polycaprolactone, poly(lactide-co-glycolide), poly(lactide-co-caprolactone), poly(lactide-co-p-dioxanone), polyorthoesters, polyanhydrides, poly(amino acid) and polycarbonates.

2. The composition of claim 1, wherein said hydrophilic polyalkylene glycol block and said hydrophobic biodegradable polymer block have molecular weights of 500 to 20,000 Daltons, respectively.

3. The composition according to claim 1, wherein the content of said amphiphilic diblock copolymer is within the range of 3 to 70% by weight based on the total weight of the composition.

4. The composition according to claim 1, wherein said poorly water-soluble drug is selected from the group consisting of anticancer agents, antifungal agents, steroids, anti-inflammatory agents, sex hormones, immunosuppressants, antiviral agents, anesthetics, anti-emetics and antihistamines, having solubilities in water of 10 mg/ml or less at ambient temperatures.

5. The composition of claim 4, wherein said poorly water-soluble drug is a member selected from the group consisting of paclitaxel, docetaxel, doxorubicin, cisplatin, carboplatin, 5-FU, etoposide, camptothecin, testosterone, estrogen, estradiol, triamcinolone acetonide, hydrocortisone, dexamethasone, prednisolone, betamethasone, cyclosporines and prostaglandins.

6. The composition according to claim 1, wherein the content of said poorly water-soluble drug is within the range of 0.1 to 50% by weight based on the total weight of the amphiphilic diblock copolymer.

7. The composition according to claim 1, wherein said biodegradable polymer is a polylactide, polycaprolactone or poly(lactide-co-glycolide), or a mixture thereof.

8. The composition according to claim 1, wherein the content of the biodegradable polymer is within the range of 5 to 80% by weight based on the total weight of the composition.

9. The composition according to claim 1, wherein said biodegradable polymer has a molecular weight of 500 to 50,000 Daltons.

10. The composition of claim 1, wherein the content of the liquid poly(ethylene glycol) is within the range of 5 to 80% by weight based on the total weight of the composition.

11. The composition according to claim 1, wherein said liquid poly(ethylene glycol) has a molecular weight of 100 to 3,000 Daltons.

12. The composition according to claim 1, wherein said liquid poly(ethylene glycol) is an alkyl or allyl derivative of poly(ethylene glycol).

13. A liquid polymeric composition for the sustained delivery of a poorly water-soluble drug comprising:
i) 3 to 70 wt % based on the total weight of the composition of an amphiphilic diblock copolymer;
ii) 0.1 to 50 wt % based on the total weight of the amphiphilic diblock copolymer of a poorly water-soluble drug;
iii) 5 to 80 wt % based on the total weight of the composition a biodegradable polymer; and,
iv) 5 to 80 wt % based on the total weight of the composition of liquid poly(ethylene glycol); wherein said amphiphilic diblock copolymer, said poorly water-soluble drug and said biodegradable polymer are dissolved or dispersed in said liquid poly(ethylene glycol); and wherein said composition is an injectable liquid at a room temperature and, upon being injected into a body, forms an implant containing polymeric micelles wherein said poorly water-soluble drugs are physically trapped and wherein said amphiphilic diblock copolymer is composed of a hydrophilic polyalkylene glycol block selected from the group consisting of polyethylene glycol, monoalkoxypolyethylene glycol and monoacyloxypolyethylene glycol and a hydrophobic biodegradable polymer block selected from the group consisting of polylactides, polycaprolactone, poly(lactide-co-glycolide), poly(lactide-co-caprolactone), poly(lactide-co-p-dioxanone), polyorthoesters, polyanhydrides, poly(amino acid) and polycarbonates.

14. The composition according to claim 13, wherein said amphiphilic diblock copolymer is composed of a hydrophilic polyalkylene glycol block and a hydrophobic biodegradable polymer block having molecular weights of 500 to 20,000 Daltons, respectively.

15. The composition according to claim 13, wherein said poorly water-soluble drug is selected from the group consisting of anticancer agents, antifungal agents, steroids, anti-inflammatory agents, sex hormones, immunosuppressants, antiviral agents, anesthetics, anti-emetics and antihistamines, having solubilities in water of 10 mg/ml or less at ambient temperatures.

16. The composition of claim 15, wherein said poorly water-soluble drug is a member selected from the group consisting of paclitaxel, docetaxel, doxorubicin, cisplatin, carboplatin, 5-FU, etoposide, camptothecin, testosterone, estrogen, estradiol, triamcinolone acetonide, hydrocortisone, dexamethasone, prednisolone, betamethasone, cyclosporines and prostaglandins.

17. The composition according to claim 13, wherein said biodegradable polymer is a member selected from the group consisting of polylactide, polycaprolactone, poly(lactide-co-glycolide) and a mixture thereof and has a molecular weight of 500 to 50,000 Daltons.

18. The composition according to claim 13, wherein said liquid poly(ethylene glycol) has a molecular weight of 100 to 3,000 Daltons and is an alkyl or allyl derivative of poly(ethylene glycol).

19. A process for preparing the composition according to claim 1, comprising the steps of:
i) mixing liquid polyethylene glycol, an amphiphilic diblock copolymer and a poorly water-soluble drug to form a polymeric micellar polyethylene glycol liquid composition;
ii) dissolving or dispersing a biodegradable polymer in liquid poly(ethylene glycol) to form a biodegradable polymer liquid composition; and
iii) mixing together said liquid compositions of steps i) and ii).

20. The process according to claim 19, wherein said amphiphilic diblock copolymer is composed of a hydrophilic polyalkylene glycol block and a hydrophobic biodegradable polymer block.

21. The process according to claim 20, wherein said hydrophilic polyalkylene glycol block is a member selected from the group consisting of polyethylene glycol, monoalkoxypolyethylene glycol and monoacyloxypolyethylene glycol, and said hydrophobic biodegradable polymer block is a member selected from the group consisting of polylactides, polycaprolactone, poly(lactide-co-glycolide), poly(lactide-co-caprolactone), poly(lactide-co-p-dioxanone), polyorthoesters, polyanhydrides, poly(amino acid) and polycarbonates.

22. The process of claim 21, wherein said hydrophilic polyalkylene glycol block and said hydrophobic biodegradable polymer block have molecular weights of 500 to 20,000 Daltons, respectively.

23. The process according to claim 19, wherein the content of said amphiphilic diblock copolymer is within the range of 3 to 70% by weight based on the total weight of the composition.

24. The process according to claim 19, wherein said poorly water-soluble drug is selected from the group consisting of anticancer agents, antifungal agents, steroids, anti-inflammatory agents, sex hormones, immunosuppressants, antiviral agents, anesthetics, anti-emetics and antihistamines, having solubilities in water of 10 mg/ml or less at ambient temperatures.

25. The process of claim 24, wherein said poorly water-soluble drug is a member selected from the group consisting of paclitaxel, docetaxel, doxorubicin, cisplatin, carboplatin, 5-FU, etoposide, camptothecin, testosterone, estrogen, estradiol, triamcinolone acetonide, hydrocortisone, dexamethasone, prednisolone, betamethasone, cyclosporines and prostaglandins.

26. The process according to claim 19, wherein the content of said poorly water-soluble drug is within the range of 0.1 to 50% by weight based on the total weight of the amphiphilic diblock copolymer.

27. The process according to claim 19, wherein said biodegradable polymer is a polylactide, polycaprolactone or poly(lactide-co-glycolide), or a mixture thereof.

28. The process according to claim 19, wherein the content of the biodegradable polymer is within the range of 5 to 80% by weight based on the total weight of the composition.

29. The process according to claim 19, wherein said biodegradable polymer has a molecular weight of 500 to 50,000 Daltons.

30. The process of claim 19, wherein the content of the liquid poly(ethylene glycol) is within the range of 5 to 80% by weight based on the total weight of the composition.

31. The process according to claim 19, wherein said liquid poly(ethylene glycol) has a molecular weight of 100 to 3,000 Daltons.

32. The process according to claim 19, wherein said liquid poly(ethylene glycol) is an alkyl or allyl derivative of poly(ethylene glycol).

33. A process for preparing the composition according to claim 13, comprising the steps of:
i) mixing liquid polyethylene glycol, an amphiphilic diblock copolymer and a poorly water-soluble drug to form a polymeric micellar polyethylene glycol liquid composition;
ii) dissolving or dispersing a biodegradable polymer in liquid poly(ethylene glycol) to form a biodegradable polymer liquid composition; and
iii) mixing together said liquid compositions of steps i) and ii).

34. The process according to claim 33, wherein said amphiphilic diblock copolymer is composed of a hydrophilic polyalkylene glycol block and a hydrophobic biodegradable polymer block having molecular weights of 500 to 20,000 Daltons, respectively.

35. The process according to claim 34, wherein said hydrophilic polyalkylene glycol block is a member selected from the group consisting of polyethylene glycol, monoalkoxypolyethylene glycol and monoacyloxypolyethylene glycol, and said hydrophobic biodegradable polymer block is a member selected from the group consisting of polylactides, polycaprolactone, poly(lactide-co-glycolide), poly(lactide-co-caprolactone), poly(lactide-co-p-dioxanone), polyorthoesters, polyahhydrides, poly(amino acid) and polycarbonates.

36. The process according to claim 33, wherein said poorly water-soluble drug is selected from the group consisting of anticancer agents, antifungal agents, steroids, anti-inflammatory agents, sex hormones, immunosuppressants, antiviral agents, anesthetics, anti-emetics and antihistamines, having solubilities in water of 10 mg/ml or less at ambient temperatures.

37. The process of claim 36, wherein said poorly water-soluble drug is a member selected from the group consisting of paclitaxel, docetaxel, doxorubicin, cisplatin, carboplatin, 5-FU, etoposide, camptothecin, testosterone, estrogen, estradiol, triamcinolone acetonide, hydrocortisone, dexamethasone, prednisolone, betamethasone, cyclosporines and prostaglandins.

38. The process according to claim 33, wherein said biodegradable polymer is a member selected from the group consisting of polylactide, polycaprolactone, poly(lactide-co-glycolide) and a mixture thereof and has a molecular weight of 500 to 50,000 Daltons.

39. The process according to claim 33, wherein said liquid poly(ethylene glycol) has a molecular weight of 100 to 3,000 Daltons and is an alkyl or allyl derivative of poly(ethylene glycol).

40. A method for the sustained delivery of a poorly water-soluble drug to a warm blooded animal comprising preparing the composition according to claim 1 by
i) mixing liquid polyethylene glycol, an amphiphilic diblock copolymer and a poorly water-soluble drug to form a polymeric micellar polyethylene glycol liquid composition;
ii) dissolving or dispersing a biodegradable polymer in liquid poly(ethylene glycol) to form a biodegradable polymer liquid composition; and
iii) mixing together said liquid compositions of steps i) and ii); and administering the liquid composition to said warm blooded animal.

* * * * *